US010591456B2

(12) United States Patent
Song

(10) Patent No.: US 10,591,456 B2
(45) Date of Patent: Mar. 17, 2020

(54) IN SITU MONITORING OF COKE MORPHOLOGY IN A DELAYED COKER USING AC IMPEDANCE

(71) Applicant: ExxonMobil Research and Engineering Company, Annandale, NJ (US)

(72) Inventor: Limin Song, West Windsor, NJ (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 121 days.

(21) Appl. No.: 15/453,071

(22) Filed: Mar. 8, 2017

(65) Prior Publication Data
US 2017/0284991 A1 Oct. 5, 2017

Related U.S. Application Data

(60) Provisional application No. 62/315,302, filed on Mar. 30, 2016.

(51) Int. Cl.
C10B 55/00 (2006.01)
G01N 33/22 (2006.01)
(Continued)

(52) U.S. Cl.
CPC .......... G01N 33/222 (2013.01); C10B 41/00 (2013.01); C10B 45/00 (2013.01); C10B 55/00 (2013.01); C10G 9/005 (2013.01)

(58) Field of Classification Search
CPC ......... C10B 55/00; C10B 55/02; C10B 55/04; C10B 55/06; C10B 55/08; C10B 55/10; C10G 9/005; C10G 2300/708
See application file for complete search history.

(56) References Cited

U.S. PATENT DOCUMENTS 7,374,665 B2    5/2008 Eppig et al.
7,727,382 B2 *  6/2010 Sparks .................. C10B 25/10
                                                  208/131
(Continued)

FOREIGN PATENT DOCUMENTS

WO    03/048271 A1    6/2003
WO    2004/104139 A1  12/2004
(Continued)

OTHER PUBLICATIONS

Muller et al., "In situ Monitoring of Coke Deposits during Coking and Regeneration of Solid Catalysts by Electrical Impedance-based Sensors", Chemical Engineering and Technology, 2010, 33, No. 1, 103-112 (Year: 2010).*

(Continued)

Primary Examiner — Jonathan Luke Pilcher
(74) Attorney, Agent, or Firm — Hsin Lin; Andrew T. Ward

(57) ABSTRACT

Methods and systems for in situ monitoring of coke morphology in a delayed coking unit. At least one transmitting electrode and at least one receiving electrode are utilized to transmit AC current across coke being formed within the delayed coking unit. An impedance analyzer can be used to measure the impedance encountered between the transmitting electrode and the receiving electrode. This measure impedance is compared to an impedance curve comprising known impedance values for different coke morphologies to determine the morphology of coke being formed in the delayed coking unit.

8 Claims, 4 Drawing Sheets

(51) Int. Cl.
*C10G 9/00* (2006.01)
*C10B 45/00* (2006.01)
*C10B 41/00* (2006.01)

(56) References Cited

U.S. PATENT DOCUMENTS

| | | | |
|---|---|---|---|
| 7,871,510 B2 | 1/2011 | Leta et al. | |
| 7,940,298 B2 * | 5/2011 | Clark | H04N 7/18 |
| | | | 348/125 |
| 8,436,898 B1 * | 5/2013 | Clark | H04N 7/18 |
| | | | 348/125 |
| 9,052,230 B2 * | 6/2015 | Kutlik | G01H 3/125 |
| 9,829,368 B2 * | 11/2017 | Kutlik | G01H 3/125 |
| 2005/0269247 A1 * | 12/2005 | Sparks | C10B 25/10 |
| | | | 208/131 |
| 2006/0196811 A1 * | 9/2006 | Eppig | B01D 19/0078 |
| | | | 208/131 |
| 2010/0007729 A1 * | 1/2010 | Clark | H04N 7/18 |
| | | | 348/125 |
| 2012/0287749 A1 * | 11/2012 | Kutlik | G01H 3/125 |
| | | | 367/7 |
| 2012/0298553 A1 * | 11/2012 | Fern | C10B 55/00 |
| | | | 208/106 |
| 2015/0329784 A1 | 11/2015 | Siskin et al. | |

FOREIGN PATENT DOCUMENTS

| | | |
|---|---|---|
| WO | 2005/113708 A1 | 12/2005 |
| WO | 2005/113709 A1 | 12/2005 |
| WO | 2005/113710 A1 | 12/2005 |
| WO | 2005/113711 A1 | 12/2005 |
| WO | 2005/113712 A1 | 12/2005 |
| WO | 2007/050350 A1 | 5/2007 |
| WO | 2007/058750 A1 | 5/2007 |

OTHER PUBLICATIONS

Guo, Aijun et al., "Investigation on shot-coke-forming propensity and controlling of coke morphology during heavy oil raking", Fuel Processing Technology, 2012, vol. 104, pp. 332-342.

Kelemen, S.R. et al., "Delayed Coker Coke Morphology Fundamentals: Mechanistic Implications Based on XPS Analysis of the Composition of Vanadium-and Nickel-Containing Additives during Coke Formation", Energy & Fuels, 2007, vol. 21, pp. 927-940.

Siskin, M. et al., "Asphaltene Molecular Structure and Chemical Influences on the Morphology of Coke Produced in Delayed Coking", Energy & Fuels, 2006, vol. 20, pp. 1227-1234.

Siskin, M. et al., "Chemical Approach to Control Morphology of Coke Produced in Delayed Coking", Energy & Fuels, 2006, vol. 20, pp. 2117-2124.

* cited by examiner

IN SITU MONITORING OF COKE MORPHOLOGY IN A DELAYED COKER USING AC IMPEDANCE

CROSS-REFERENCE TO RELATED APPLICATIONS

This application claims priority to U.S. Provisional Application Ser. No. 62/315,302 filed Mar. 30, 2016, which is herein incorporated by reference in its entirety.

FIELD

Methods and systems are provided for in situ monitoring of coke morphology in a delayed coker using AC impedance.

BACKGROUND

A coker unit is an oil refinery processing unit that converts residual oil from a separate oil refinery processing unit, such as a vacuum distillation column or an atmospheric distillation column, into low molecular weight hydrocarbon gases, naphtha, light and heavy gas oils, and petroleum coke. A coker unit uses heat to thermally crack long chain hydrocarbon molecules in is the residual oil feed into shorter chain molecules. The byproduct of this process is petroleum coke (or "coke").

One type of coker unit is a delayed coker. A delayed coker is typically comprised of a main fractionator, a heat source, and at least one pair of coke drums. Residual oil feed from a separate refinery processing unit is pumped into the bottom of the main fractionator, which essentially is a distillation column. From there it is pumped, along with some injected steam to a furnace and heated to its thermal cracking temperature. It is then transported to one of the two coke drums where the majority of thermal cracking takes place. Lighter components are generated in vapor phase and directed back to the main fractionator where it is separated into various boiling point fractions. Coke remains in the coke drum. Once the first coke drum is filled with solid coke, the residual oil feed is directed from the furnace to the second coke drum. While the second coke drum is filling, coke from in the first coke drum is removed. Removal of the coke typically consists of quenching the coke with water to cool it followed by removing the top and bottom heads of the coke drum. Solid coke is then cut from the coke drum with a high pressure water jet. It then falls into a designated area for reclamation or storage.

Delayed coking is an important but slow process. One cycle generally takes more than ten hours to complete. This can create a bottleneck for other refinery processes. Reducing the delayed coker cycle time will increase throughput and in turn increase efficiency of the delayed coker and the refinery as a whole.

Delayed coking produces different types of cokes—i.e. coke with different morphology. Selected aromatic feedstocks may be used in the delayed coking process to produce high-quality needle cokes for graphite production. More commonly, though, more porous coke is produced. This more porous coke comes in predominantly two morphologies: (1) sponge coke and (2) shot coke. Generally, shot coke is preferred to sponge coke because it is more easily removed from the coke drum. Because it is more easily removed from the coke drum, the formation of shot coke can reduce delayed coking cycle times and ultimately improve refinery efficiency. Additionally, sponge coke can generally lead to "hot spots" within the coke drum which causes safety concerns during the coke removal process.

The mechanisms that produce sponge or shot coke are still not well understood in the industry. One technique involves measuring the ratio of the microcarbon residue (hereinafter "MCR") to the quantity of asphaltenes present in the resid. If this ratio is less than 2, the resid will produce primarily shot coke. If the ratio is higher than 2, the resid will produce primarily sponge coke. The MCR to asphaltene ratio is based upon historical plant experience, but this ratio is only accurate at the extremes of the morphology spectrum and not at the intermediate values that are typically found in refineries.

A second approach found in the literature is to experimentally measure the quantity of aromatic carbon and heteroatoms (O, S, N) present in a precipitated asphaltene sample. If the ratio is greater than 11 then primarily sponge coke will be formed and if the ratio is less than 7 primarily shot coke will be formed. The region between 7 and 11 is a transitional region where the coke can create hot spots. This technique does not quantify the intermediate resids processed at some refineries, and the analysis is difficult to perform in a timely manner without specialized equipment. Furthermore, each of these techniques add an additional error to the measurement because the resid suspension is broken to remove the asphaltene molecules for analysis.

U.S. Publication No. 2015/0329784 to Siskin et al. takes a chemical approach to controlling coke morphology. The process comprises, in summary, mixing asphaltene derived from a shot coke-forming petroleum residual feed with or into a heated sponge coke forming petroleum residual feed to form shot coke directing asphaltene aggregates in the resid, holding the mixture of resid and the asphaltenes aggregates at an elevated temperature to allow co-aggregates of sponge coke and shot coke asphaltenes to form, and heating the heated resid containing the co-aggregates to a delayed coking temperature to form shot coke and thermally cracked coker products.

Other articles in the technical literature by Siskin and Kelemen together with their colleagues have provided insights into the possibilities of controlling coke morphology. See, for example. Siskin et al, "Asphaltene Molecular Structure and Chemical Influences on the Morphology of Coke Produced in Delayed Coking", *Energy & Fuels* 2006, 20, 1227-1234; Siskin et al, "Chemical Approach to Control Morphology of Coke Produced in Delayed Coking," *Energy & Fuels*, 2006, 20, 2117-2124; Kelemen et al, "Delayed Coker Coke Morphology Fundamentals: MeChanistic Implications Based on XPS Analysis of the Composition of Vanadium and Nickel-Containing Additives During Coke Formation," *Energy & Fuels* 2007, 21, 927-940. In addition, a series of patents and applications from ExxonMobil Research and Engineering Company presented different proposals for promoting the production of a free-flowing shot coke during the delayed coking process; publications of these include U.S. Pat. Nos. 7,374,665; 7,871,510; WO 03/048271; WO 2007/050350; WO 2004/104139; WO 2005/113711; WO 2005/113712; WO 2005/113710; WO 2005/113709; WO 2005/113709; WO 2005/113708; WO 2007/058750.

Still others have observed changes in coke morphology with various operating parameters of the delayed coker—e.g. feed rate, pressure, and temperature, See, e.g. Michael Volk et al., *Fundamentals of Delayed Coking Joint Industry Project*, Univ. of Tulsa (2005). Other parameters that have been found to have an effect on coke morphology are recycle ratio and providing hydrogen donating additives to the feedstock, See, e.g., Aijun Guo et al., "Investigation on shot-coke-forming propensity and controlling of coke morphology during heavy oil coking," 104 *Fuel Processing Tech.* 332 (2012).

While each of these publication describe factors that one may use to effect coke morphology, the number of variables present in the real world make such methods impractical. To truly ensure that the delayed coking process forms the preferred coke morphology, there is a need to monitor the coke morphology in situ while the coke is being made. Acoustic methods have been studied which show that attenuation and sonic speed can be correlated with coke morphology. However, the attenuation in using such methods is too high for field application. The currently disclosed process measures the AC impedance of the coke between one or more pairs of electrodes and determines coke morphology (e.g. sponge coke vs. shot coke) by using a correlation between coke morphology and AC impedance.

SUMMARY

In various aspects, methods and systems are provided for monitoring coke morphology in situ in a delayed coking unit containing coke, comprising providing a transmitting electrode; providing a receiving electrode; transmitting an AC current at a frequency from the transmitting electrode to the receiving electrode; measuring an impedance between the transmitting electrode and the receiving electrode across the coke at the frequency; and comparing the measured impedance to an impedance curve to determine the coke morphology within the delayed coking unit. In one aspect, the transmitting and receiving electrodes are located within the delayed coking unit.

In certain aspects, the methods and systems can include providing at least one additional transmitting and/or receiving electrode. These electrodes may operate in pairs or there may be more than one transmitting electrode for each receiving electrode or there may be more than one receiving electrode for each transmitting electrode.

Additionally, the methods provided herein can include transmitting an AC current at at least one additional frequency from the transmitting electrode to the receiving electrode. The frequency is usually between 10-10,000 Hz, e.g. 10-1,000 Hz.

In another aspect, the impedance curve provides impedance values of shot-like coke and sponge-like coke in wet and dry conditions. The impedance curve can be developed based on laboratory data or based on the specific delayed coking unit or delayed coking unit design using real world data.

In yet another aspect, the method can include adjusting a feed composition into the delayed coking unit or adjusting an operating parameter (such as temperature, pressure, and recycle ratio) of the delayed coking unit to alter the coke morphology within the delayed coking unit.

Also provided is a system for monitoring coke morphology in situ in a delayed coking unit containing coke, comprising: a transmitting electrode; a receiving electrode; a source of AC current at a frequency from the transmitting electrode to the receiving electrode; wherein the AC current traverses the coke within the delayed coking unit and an impedance analyzer to measure the impedance between the transmitting electrode and the receiving electrode across the coke at the frequency.

In one aspect, the system includes a computer, wherein the computer includes software for comparing the measured impedance between the transmitting electrode and the receiving electrode across the coke at the frequency and an impedance curve. The computer may also further include software for making a determination about the type of coke being formed in the delayed coking unit based on the comparison of the measured impedance and the impedance curve.

DETAILED DESCRIPTION

Figure 2:
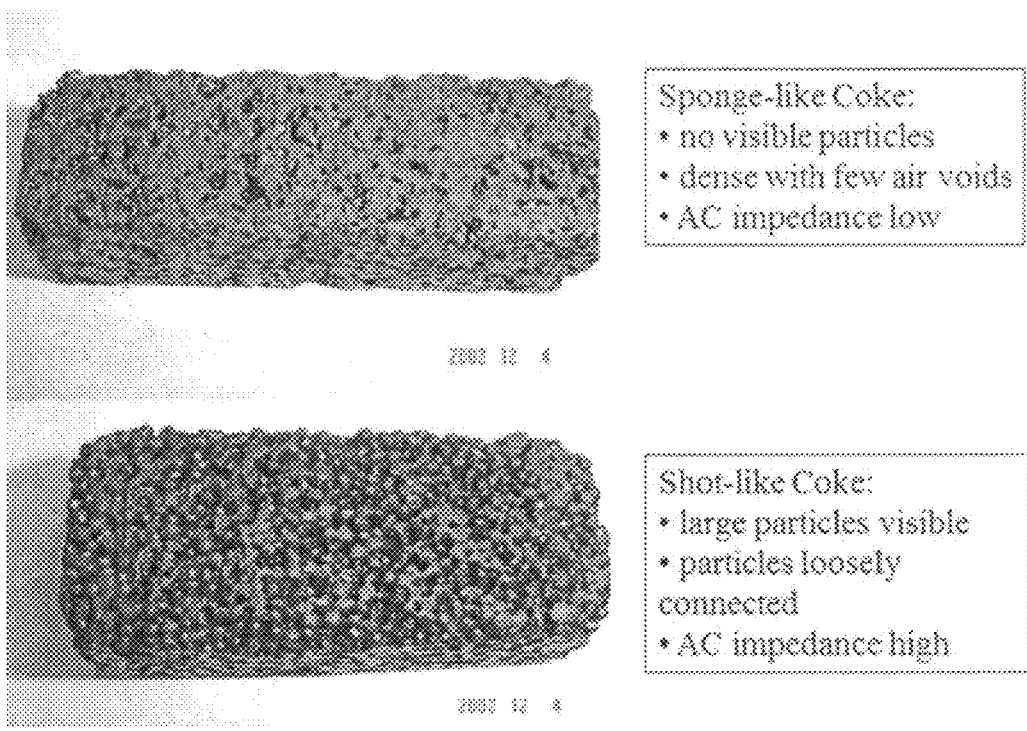
FIG. 2 is a depiction of sponge coke (top) and shot coke (bottom).

In various aspects, methods and systems are provided for in situ monitoring of coke morphology using AC impedance. As discussed above, when coke is formed during the delayed coking process, it predominantly exists in two types—sponge coke and shot coke. In many cases, refineries would prefer to make shot coke over sponge coke. As shown in FIG. 2, shot coke (bottom) forms large visible particles. These particles are loosely connected to one another. During the quench and removal process, it is easier remove shot coke from the coke drum because of these characteristics. The coke is likely to flow more easily with less water cutting or perhaps to no water cutting at all. Sponge coke (FIG. 2, top) on the other hand, generally has no visible particles and is dense with few air voids. Sponge coke can be much more difficult to remove from the coke drum. This results in increased delayed coker cycle times, which results in lower throughput and a decrease in overall refinery efficiency. Moreover, sponge coke has the potential to create hot spots within the coke drum. The existence of such hot spots necessitate very careful is cutting and removal to ensure safety.

It has been found that sponge coke and shot coke have present different impedance to AC current presumably as a result of their different morphologies. Impedance is the effective resistance of an electric circuit or component to alternating current, arising from the combined effects of ohmic resistance and reactance. If one is familiar with the impedance signature of a particular type of coke, monitoring of the impedance signature of the coke in the coke drum in situ, can provide a useful predictor of the type of coke being formed in the coke drum. Once the type of coke being formed is known, then adjustments can be made to either the feed composition and/or operating parameters of the delayed coking process to alter the coke formed to a more desirable morphology if needed.

In various aspects, a method for monitoring coke morphology in situ in a delayed coking unit containing coke is provided. In one aspect, the method includes providing a transmitting electrode. The transmitting electrode may be located within the delayed coking unit. The transmitting electrode transmits AC current at a given frequency through the coke being formed in the drum. In another aspect, the method includes providing a receiving electrode, which may be located within the delayed coking unit. The receiving electrode receives the AC current provides from the transmitting electrode. The impedance between the transmitting electrode and the receiving electrode can then be measured by any method known in the art. There may be multiple transmitting electrodes and multiple receiving electrodes. The transmitting electrodes and receiving electrodes may operate in pairs—i.e. one transmitting electrode for every receiving electrode—or there may be one or more receiving electrode for each transmitting electrode or more than one transmitting electrode each receiving electrode. For example, if the spatial distribution of coke morphology is of interest, then it may be advantageous to have a single transmitting electrode and many receiving electrodes distributed within the coke drum to obtain impedance, and in turn morphology, information along the path between the transmitting electrode and each receiver. It is possible, however, that the signal attenuation with such a configuration could become an issue. That is, the signal may fade if the distance between the transmitting electrode and the receiving electrode is too great. This issue could be solved using transmitting electrodes so that no distance between a particular transmitting electrode or receiving electrode is too great.

The transmitting electrode may transmit current at a single frequency or varying frequencies, for example, between 10 Hz and 10,000 Hz or between 10 Hz and 1,000 Hz. Analysis at multiple frequencies allows additional data analysis such as curve fitting to improve accuracy and robustness of coke morphology classification.

Figure 3:
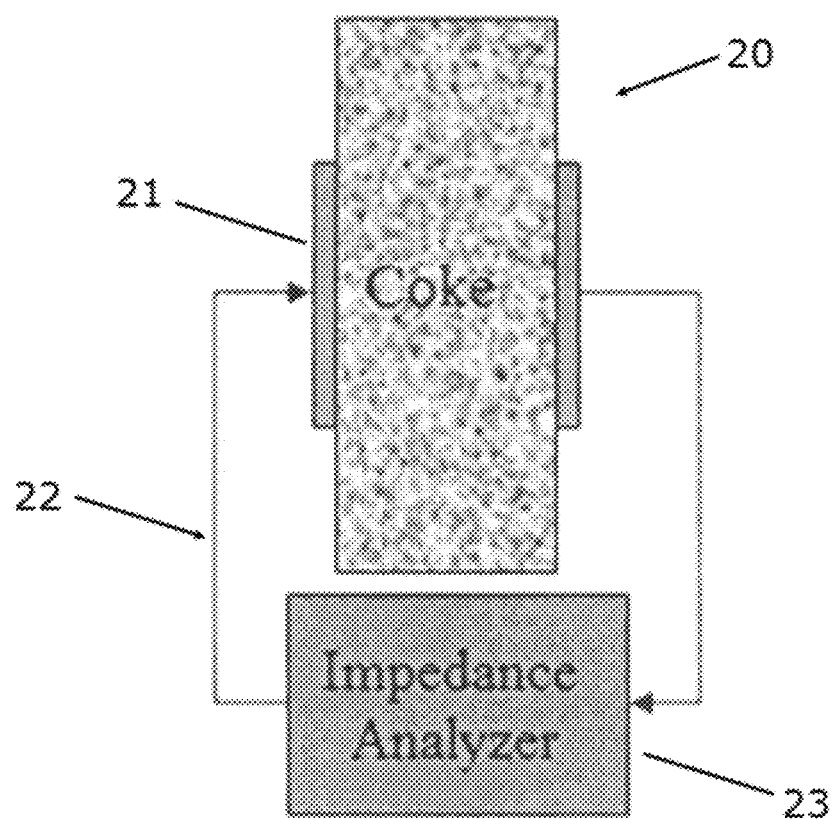
FIG. 3 schematically illustrates a laboratory experimental setup used to develop impedance curves for use in the process disclosed herein.
Figure 4:
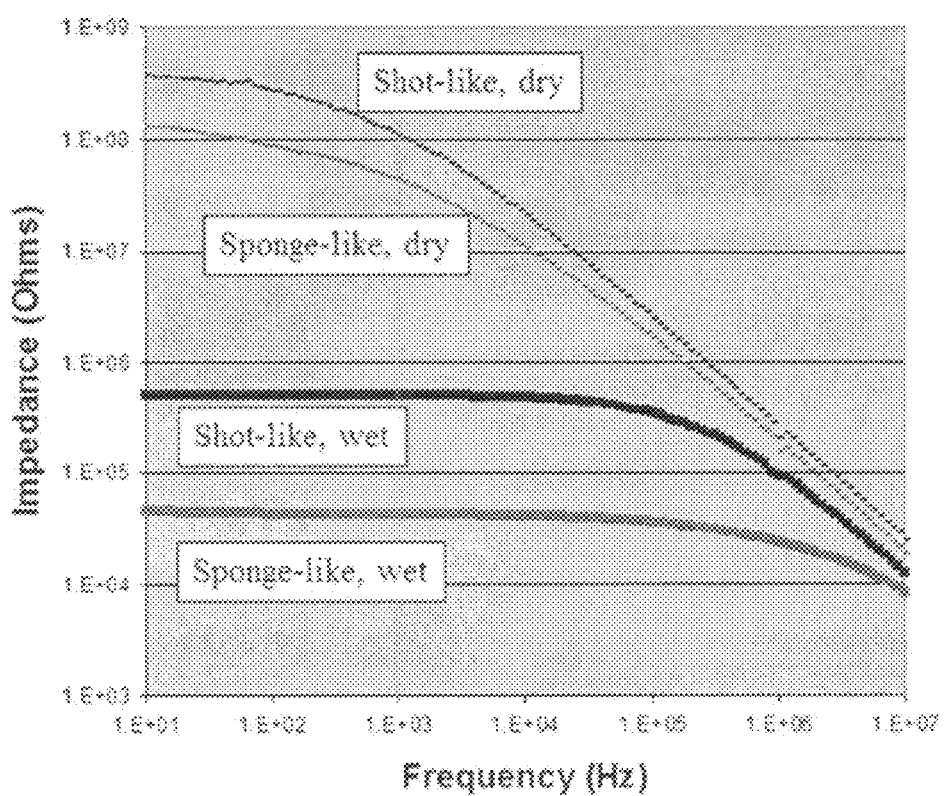
FIG. 4 illustrates impedance curves developed for use in the process disclosed herein.

In another aspect, the methods and systems provided herein include comparing the is measured impedance from the transmitting electrode(s) to the receiving electrode(s) to an impedance curve to determine the coke morphology within the delayed coking unit. Impedance curves can be developed in a laboratory. One such experimental setup is illustrated in FIGS. 3 and 4. In laboratory setup 20, a vessel is filled with various types of coke to develop impedance curves for different morphologies of coke. In this particular experiment as shown in FIG. 4, impedance curves are shown for dry shot coke, wet shot coke, dry sponge coke, and wet sponge coke. AC Voltage 21 is applied across the vessel containing the coke with the specific morphology. AC Current 22 is then formed and the impedance is measured across impedance analyzer 23. As can be seen from FIG. 4, the impedance of shot coke is higher than the impedance of sponge coke and the impedance of dry coke is higher than the impedance of wet coke. This differences can be observed at varying frequencies to develop a more complete impedance curve for varying coke morphologies. A preferred frequency of 10-10,000 Hz is adequate for separating the various coke morphologies.

In another aspect, impedance curves may be developed for a specific coking unit or coking unit design. These impedance curves would be developed empirically based on the morphology of coke formed during real time operation of the coker. In essence, this type of impedance curve is formed the same way as the laboratory set-up described above except the coke morphology would not be known until observed after its formation in the coker.

In yet another aspect, a system for in situ monitoring of coke morphology is provided. The system consists of a delayed coking unit containing coke, a transmitting electrode, a receiving electrode, and a source of AC current, wherein the AC current traverses the coke within the delayed coking unit, and an impedance analyzer to measure the impedance between the transmitting electrode and the receiving electrode across the coke at the frequency. There may be multiple transmitting electrodes and multiple receiving electrodes. The transmitting electrodes and receiving electrodes may operate in pairs—i.e. one transmitting electrode for every receiving electrode—or there may be one or more receiving electrode for each transmitting electrode or more than one transmitting electrode each receiving electrode.

As described in reference to the method above, it is helpful to compare the measured impedance across the coke to an impedance curve to determine coke morphology. Accordingly, in another aspect the system includes a computer equipped with software for comparing the measured impedance between the transmitting electrode and the receiving electrode across the coke at the frequency and an impedance curve. The computer may further include software for making a determination about the type of coke being formed in the delayed coking unit based on the comparison of the measured impedance and the impedance curve.

Figure 1:
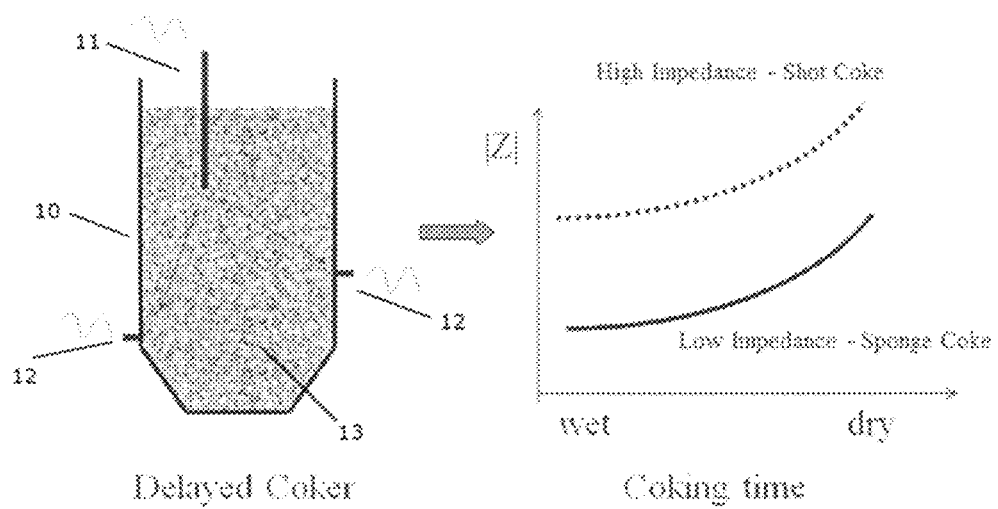
FIG. 1 schematically illustrates a general diagram of the AC impedance processes and systems disclosed herein.

FIG. 1 illustrates one possible implementation of the method and system. Delayed coker 10 is in service is filling up with coke 13. Transmitting electrode 11 transmits AC current at a given frequency or a set of different frequencies. The current is received by receiving electrodes 12. The impedance is measured and compared to an impedance curve for various coke morphologies. As can be seen by the graph on the right hand side of FIG. 1, the impedance of shot coke tends to be higher than that of sponge coke and each morphology (sponge and shot) have a higher impedance when wet rather than dry. As coking time increases, the coke tends to dry out and impedance increases for either type of morphology.

Once the coke morphology is known, refineries can take the proper action to determine ensure that the delayed coking process is forming coke of the desired morphology. For example, the adjustments can be made to the feedstock entering the delayed coking unit. Such adjustments can include providing hydrogen donating additives to the feed and/or adjusting the proportion of feed prone to shot coke formation with feed prone to sponge coke formation. Moreover, adjustments can be made to the operating parameters of the delayed coking unit itself. Such adjustments can include changes to temperature, pressure, and recycle ratio. Recycle ratio is the ratio of liquid product recirculated back to reaction zone within the coking unit. These adjustments are not an exclusive list and other adjustments to the feedstock or operating parameters can have an effect on coke morphology.

ADDITIONAL EMBODIMENTS

Embodiment 1

A method for monitoring coke morphology in situ in a delayed coking unit containing coke, comprising providing a transmitting electrode; providing a receiving electrode; transmitting an AC current at a frequency from the transmitting electrode to the receiving electrode; measuring an impedance between the transmitting electrode and the receiving electrode across the coke at the frequency; and comparing the measured impedance to an impedance curve to determine the coke morphology within the delayed coking unit.

Embodiment 2

The method of embodiment 1, further comprising providing at east one additional receiving electrode within the delayed coking unit.

Embodiment 3

The method of any of the previous embodiments, further comprising at least one additional transmitting electrode.

Embodiment 4

The method of any of the previous embodiments, wherein the transmitting electrode and receiving electrode are located within the delayed coking unit.

Embodiment 5

The method of any of the previous embodiments, further comprising at is least one additional transmitting electrode, wherein each transmitting and receiving electrode are operated in pairs.

Embodiment 6

The method of any of the previous embodiments, further comprising transmitting an AC current at at least one additional frequency from the transmitting electrode to the receiving electrode.

Embodiment 7

The method of any of the previous embodiments, wherein the frequency is between 10-10,000 Hz.

Embodiment 8

The method of any of the previous embodiments, wherein the frequency is between 10-1,000 Hz.

Embodiment 9

The method of any of the previous embodiments, wherein the impedance curve provides impedance values of shot-like coke and sponge-like coke in wet and dry conditions.

Embodiment 10

The method of any of the previous embodiments, wherein the impedance curve is developed based on laboratory data.

Embodiment 11

The method of any of the previous embodiments, wherein the impedance curve is developed based on the specific delayed coking unit or delayed coking unit design.

Embodiment 12

The method of any of the previous embodiments, further comprising adjusting a feed composition into the delayed coking unit to alter the coke morphology within the delayed coking unit.

Embodiment 13

The method of any of the previous embodiments, further comprising adjusting an operating parameter of the delayed coking unit into the delayed coking unit to alter the coke morphology within the delayed coking unit.

Embodiment 14

The method of any of the previous embodiments, wherein the adjusting an operating parameter includes adjustment of one of temperature, pressure, and recycle ratio.

Embodiment 15

A system for monitoring coke morphology in situ in a delayed coking unit containing coke, comprising: a transmitting electrode; a receiving electrode; a source of AC current at a frequency from the transmitting electrode to the receiving electrode; wherein the AC to current traverses the coke within the delayed coking unit and an impedance analyzer to measure the impedance between the transmitting electrode and the receiving electrode across the coke at the frequency.

Embodiment 16

The system of embodiment 15 further comprising a computer, wherein the computer includes software for comparing the measured impedance between the transmitting is electrode and the receiving electrode across the coke at the frequency and an impedance curve.

Embodiment 17

The system of embodiment 16, wherein the computer further includes software for making a determination about the type of coke being formed in the delayed coking unit based on the comparison of the measured impedance and the impedance curve.

Embodiment 18

The system of any of embodiments 15-17, further comprising at least one additional receiving electrode.

Embodiment 19

The system of any of embodiments 15-18, further comprising at least one additional transmitting electrode.

Embodiment 20

The system of any of embodiments 15-19, wherein the transmitting electrode and receiving electrode are located within the delayed coking unit.

Embodiment 21

The system of embodiment 18, further comprising at least one additional transmitting electrode, wherein each transmitting and receiving electrode are operated in pairs.

Embodiment 22

The system of any of embodiments 16-21, wherein the impedance curve provides impedance values of shot-like coke and sponge-like coke in wet and dry conditions.

Embodiment 23

The system of any of embodiments 16-22, wherein the impedance curve is developed based on laboratory data.

Embodiment 24

The system of any of embodiments 16-23, wherein the impedance curve is developed based on the specific delayed coking unit or delayed coking unit design.

Although the present invention has been described in terms of specific embodiments, it is not so limited. Suitable alterations/modifications for operation under specific conditions should be apparent to those skilled in the art. It is therefore intended that the following claims be interpreted as covering all such alterations modifications as fall within the true spirit/scope of the invention.

The invention claimed is:

1. A system for monitoring coke morphology in situ in a delayed coking unit containing coke, comprising:
   a delayed coking unit containing coke;
   a transmitting electrode;
   a receiving electrode;
   an AC current supply, which provides an AC current at a frequency from the transmitting electrode to the receiving electrode;
   an impedance analyzer, wherein the impedance analyzer measures at least one impedance between the transmitting electrode and the receiving electrode across the coke at the AC current frequency to form a measured impedance; and
   a computer, wherein the computer is configured to compare the measured impedance between the transmitting electrode and the receiving electrode across the coke at the AC current frequency and an impedance curve;
   wherein the AC current traverses the coke within the delayed coking unit;
   wherein the at least one impedance value is used to determine the coke morphology; and
   wherein the computer is configured to make a determination about the coke morphology in the delayed coking unit based on the comparison of the measured impedance and the impedance curve.

2. The system of claim 1, further comprising at least one additional receiving electrode.

3. The system of claim 2, further comprising at least one additional transmitting electrode, wherein each transmitting and receiving electrode are operated in pairs.

4. The system of claim 1, further comprising at least one additional transmitting electrode.

5. The system of claim 1, wherein the transmitting electrode and receiving electrode are located within the delayed coking unit.

6. The system of claim 1, wherein the impedance curve provides impedance values of shot-like coke and sponge-like coke in wet and dry conditions.

7. The system of claim 1, wherein the impedance curve is developed based on laboratory data.

8. The system of claim 1, wherein the impedance curve is developed based on the specific delayed coking unit or delayed coking unit design.

* * * * *